US009267878B2

(12) United States Patent
Uchida et al.

(10) Patent No.: US 9,267,878 B2
(45) Date of Patent: Feb. 23, 2016

(54) ACOUSTIC SIGNAL RECEIVING APPARATUS AND PHOTO-ACOUSTIC TOMOGRAPHY

(71) Applicant: CANON KABUSHIKI KAISHA, Tokyo (JP)

(72) Inventors: Takeshi Uchida, Tokyo (JP); Takao Nakajima, Kyoto (JP); Takako Suga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/196,929

(22) Filed: Mar. 4, 2014

(65) Prior Publication Data
US 2014/0253927 A1  Sep. 11, 2014

(30) Foreign Application Priority Data
Mar. 6, 2013 (JP) .................................. 2013-044271

(51) Int. Cl.
| | |
|---|---|
| G01B 9/02 | (2006.01) |
| G01N 21/17 | (2006.01) |
| G01H 9/00 | (2006.01) |
| G01N 29/24 | (2006.01) |

(52) U.S. Cl.
CPC ........ *G01N 21/1702* (2013.01); *G01B 9/02007* (2013.01); *G01B 9/02027* (2013.01); *G01H 9/00* (2013.01); *G01N 29/2418* (2013.01); G01B 2290/25 (2013.01); G01B 2290/45 (2013.01)

(58) Field of Classification Search
CPC ........... G01B 9/02007; G01B 9/02027; G01B 2290/25; G01B 2290/45; G01H 9/00; G01H 9/002; G01J 3/26; G01N 21/1702; G01N 29/2418
See application file for complete search history.

(56) References Cited

U.S. PATENT DOCUMENTS

| | | | |
|---|---|---|---|
| 2007/0157730 A1* | 7/2007 | Ochiai et al. | ..................... 73/627 |
| 2009/0289198 A1* | 11/2009 | Youngner | .................. 250/458.1 |

(Continued)

FOREIGN PATENT DOCUMENTS

| | | |
|---|---|---|
| JP | 2000-151509 A | 5/2000 |

OTHER PUBLICATIONS

Edward Zhang, Jan Laufer, and Paul Beard, Backward-Mode Multiwavelength Photoacoustic Scanner Using a Planer Fabry-Perot Polymer Film Ultrasound Sensor for High-Resolution Three-Dimensional Imaging of Biological Tissues, Applied Optics, Feb. 1, 2008, 47(4):561-577, Optical Society of America, Washington DC (2008).

*Primary Examiner* — Michael A Lyons
(74) *Attorney, Agent, or Firm* — Canon USA, Inc. I.P. Division (57) ABSTRACT

An acoustic signal receiving apparatus including: a Fabry-Perot sensor including a Fabry-Perot interferometer configured to convert an acoustic wave into a light intensity signal; a control unit configured to set a first wavelength and a second wavelength; a detecting unit configured to convert light intensities obtained by irradiation of the Fabry-Perot sensor with light from the first light source and the second light source into electric signals; and a signal processing unit configured to acquire a difference between an electric signal corresponding to the first wavelength and an electric signal corresponding to the second wavelength, wherein the control unit is configured to set the first wavelength and the second wavelength so that differential values of reflectivity spectrum of the Fabry-Perot sensor are different at the first wavelength and the second wavelength.

17 Claims, 6 Drawing Sheets

(56) References Cited

U.S. PATENT DOCUMENTS

| | | | |
|---|---|---|---|
| 2012/0220844 A1* | 8/2012 | Baker, Jr. | 600/328 |
| 2013/0160557 A1* | 6/2013 | Nakajima et al. | 73/655 |
| 2014/0076055 A1* | 3/2014 | Asao et al. | 73/655 |
| 2014/0118749 A1* | 5/2014 | Nakajima et al. | 356/519 |

* cited by examiner

ACOUSTIC SIGNAL RECEIVING APPARATUS AND PHOTO-ACOUSTIC TOMOGRAPHY

BACKGROUND

1. Field of Art

This disclosure relates to an acoustic signal receiving apparatus in which a Fabry-Perot interferometer is used.

2. Description of the Related Art

Examples of known techniques of imaging an interior of a biological body include a photo-acoustic tomography (hereinafter, referred to as PAT).

The photo-acoustic tomography is configured to irradiate an object to be examined with pulsed light generated from a light source and detect acoustic waves, that are generated when energy of the pulsed light is absorbed in a biological body tissue (hereinafter, referred to as a photo-acoustic wave), at a plurality of spatial positions.

With photo-acoustic tomographic technology, signals of the acoustic waves are analyzed and processed and information such as distribution of optical energy absorption is visualized as a tomographic image.

As a method of receiving the acoustic waves such as the photo-acoustic waves described above (converting acoustic wave signals to electric signals), a technique that converts an acoustic wave signal once to a light intensity modulation and then converts the light intensity modulation to an electric signal is known (E. Zang, J. Laufer, and P. Beard, "Backward-mode multiwavelength photoacoustic scanner using a planer Fabry-Perot polymer film ultrasound sensor for high-resolution three-dimensional imaging of biological tissue", Applied Optics, 47, 4. (2008)).

As a device configured to convert an acoustic wave to a light intensity signal, a structure including a relatively soft substance interposed between two parallel reflection mirrors to allow light to resonate between the two reflection mirrors, which is generally referred to as a Fabry-Perot Interferometer (FPI) is employed.

Hereinafter, the above-described structure composed of the Fabry-Perot Interferometer including the relatively soft substance interposed between the two parallel reflection mirrors is referred to as a FPI sensor.

Subsequently, a mechanism of receiving the acoustic wave by the FPI sensor will be described.

When an acoustic wave enters the FPI sensor, the film thickness between reflector plates changes, and a resonance wavelength of the FPI sensor changes. Since the FPI sensor has a resonator construction, a plurality of dips are generated in light reflectivity viewed from above the FPI sensor at positions having the resonance wavelength. The above-described dips are generally referred to as Fabry-Perot dips.

Here, when light (herein after, referred to as probe light) different from the light that generates acoustic waves is applied to the FPI sensor, and the wavelength of the probe light is adjusted to a wavelength near the resonance dips of the reflectivity of the FPI sensor, the resonance wavelength is changed when the acoustic wave enters and, consequently, the intensity of reflected light changes.

Subsequently, the light modulated in intensity by the FPI sensor is converted into the electric signal with a photo detector, whereby the acoustic wave signal is changed to the electric signal.

Hereinafter, an acoustic signal receiving apparatus including a system of receiving an acoustic signal on the basis of the above-described method of receiving the acoustic wave is referred to as FPI-PAT.

SUMMARY

There is provided an acoustic signal receiving apparatus including: a Fabry-Perot sensor including a Fabry-Perot interferometer configured to convert an acoustic wave generated from a measurement object to a light intensity signal; a control unit configured to set a first wavelength and a second wavelength different from the first wavelength; a first light source configured to emit light having the first wavelength; a second light source configured to emit light having the second wavelength; a detecting unit configured to convert light intensities of reflected rays of light obtained by irradiation of the Fabry-Perot sensor with rays of light from the first light source and the second light source into electric signals independently by the first wavelength and the second wavelength; and a signal processing unit configured to acquire a difference between an electric signal corresponding to the first wavelength and an electric signal corresponding to the second wavelength, wherein the control unit is configured to set the first wavelength and the second wavelength so that differential values of reflectivity spectrum of the Fabry-Perot sensor are different at the first wavelength and the second wavelength.

Further features of the present invention will become apparent from the following description of exemplary embodiments with reference to the attached drawings.

DESCRIPTION OF THE EMBODIMENTS

An FPI-PAT converts an acoustic wave signal into an electric signal via an intensity change of a probe light. Therefore, when the light intensity change occurs by a factor other than the intensity change caused by the acoustic wave signal, the change may distort a primary wavelength of an acoustic wave signal.

Therefore, when the light intensity change occurs by a factor other than the intensity change caused by the acoustic wave signal, the change may distort a primary waveform of an acoustic wave signal.

For example, when optical components which constitute the FPI-PAT mechanically vibrate due to vibrations from the outside and hence a permeability of an optical system changes, the light intensity may vary as a consequence. The light intensity is also modulated by an entry of light having a wavelength close to the probe light from the outside, which results in generation of noise.

This disclosure provides an acoustic signal receiving apparatus including a Fabry-Perot Interferometer and configured to reduce a noise signal caused by a change of light intensity generated by a factor other than an acoustic wave signal.

An example of a configuration of the acoustic signal receiving apparatus employing a FPI-PAT system in which a Fabry-Perot sensor including the Fabry-Perot Interferometer according to an embodiment of this disclosure will be described below.

In this embodiment, light from a first light source and light from a second light source having two different wavelengths are simultaneously used as the rays of probe light.

After the rays of light having two different wavelengths have been modulated in intensity by the FPI sensor, the light intensities of the respective rays of light are converted into electric signals independently by a photo detector.

At this time, differential values of reflectivity spectrum (wavelength dependency of reflectivity) of the FPI sensor are set to be different at the wavelengths of the rays of probe light. For example, the wavelengths of the rays of probe light are each adapted to a wavelength at which an absolute value of a differential value of a reflectivity spectrum existing in the vicinity of a resonance dip becomes a largest value, and are set so that the differential values have opposite signs (so that inclinations of the reflectivity spectrum are opposite).

In this configuration, the greatest benefits are achieved. Specifically, reduction of noise intensity and improvement of the ratio between signal intensity and the noise are achieved.

Figure 6:
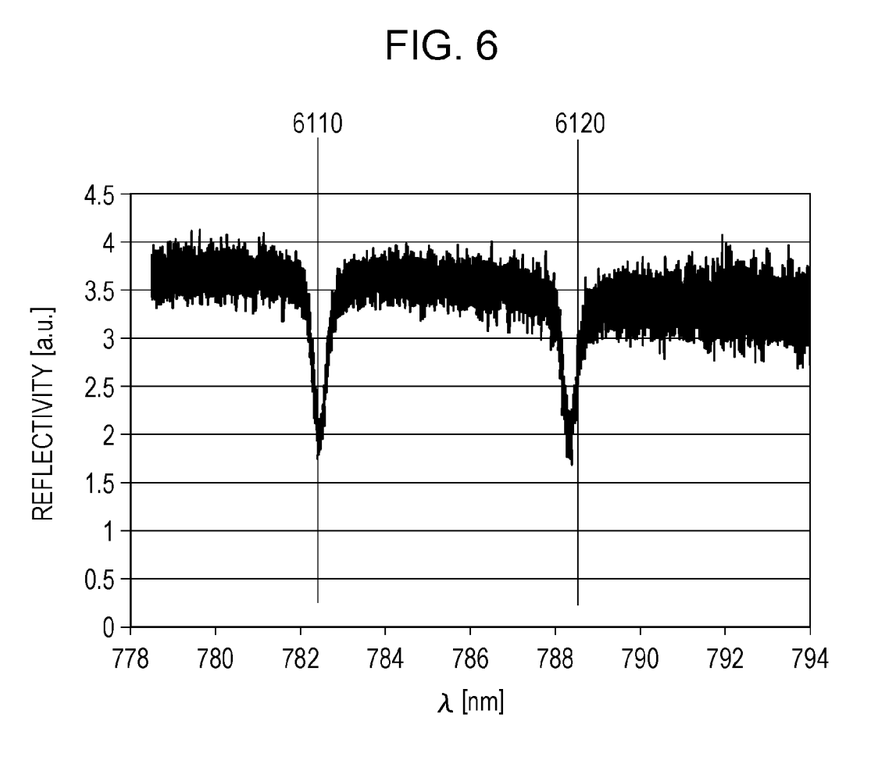
FIG. 6 is an explanatory drawing illustrating an example of setting of a reflectivity spectrum of an FPI sensor and wavelength of probe light of Exemplary Embodiments of this disclosure.

In order to explain these benefits, for example, a reflectivity spectrum of an actual FPI sensor and an example of positions where the wavelengths are set, 6110 and 6120 are illustrated in FIG. 6.

In this example, one each of the different resonance dips, specifically, 6110 is arranged at a position of 782.2 nm, and 6120 is arranged at a position of 788.4 nm.

Alternatively, 6110 and 6120 may be arranged at positions having different inclinations within the same dip.

As will be described in Exemplary Embodiment 5, the effect of reducing noise is obtained even when one of the wavelengths is arranged in an area out of the dip where the spectrum is flat.

A process of setting the wavelengths of the two rays of probe light and reducing noise signal caused by the intensity change of light caused by the factor other than the acoustic wave signal as described above will be explained further in detail.

When the two wavelengths are set to wavelengths at which the differential values in the vicinity of the resonance dip have opposite signs as described above, directions of reflectivity changes of the two rays of probe light when the acoustic wave enters the FPI sensor become opposite and, consequently, signals that are modulated in light intensity in the opposite directions are obtained.

For example, a case where the light having the first wavelength is set to a range in which the reflectivity is reduced toward a short wavelength side to a long wavelength side like 6110 in FIG. 6, and the light having the second wavelength is set to a range in which the reflectivity is increased like 6120 is assumed.

In this state, when the acoustic wave enters the FPI sensor and the length of a resonator of the FPI sensor is reduced, a resonance wavelength of the FPI sensor is shifted toward the short wavelength side.

Consequently, since the reflectivity is reduced with the first wavelength, the intensity of reflected light is reduced, and since the reflectivity is increased with the second wavelength, the intensity of reflected light is increased.

Subsequently, when the resonator changes in a direction from a contrasted state to an expanded state, the reflectivity is changed in a way opposite to the case described above. That is, with the first wavelength, the intensity of the reflected light is increased, and with the second wavelength, the intensity of the reflected light is reduced.

The most basic characteristic of the configuration in this embodiment described above is that the FPI sensor is irradiated with the two rays of probe light having different wavelengths simultaneously at positions close to each other or the same position on the Fabry-Perot sensor (on the FPI sensor) to obtain the acoustic wave signals as described above and, in addition, differential values of reflectivity spectrum of the FPI sensor are set to be different at the wavelengths of the rays of probe light. For example, the wavelengths are set so that the differential values of the FPI reflectivity spectrum have opposite signs.

The signals generated by the FPI sensor are converted into electrical signals. Then, these signals are added after one of these signals has been inverted by an electric circuit, so that noise reduction is achieved. In other words, a difference between the two electric signals corresponding to the respective wavelengths is acquired, so that noise decrease is achieved.

Reduction of noise of electric signals is known in the related art as is disclosed in Japanese Patent Laid-Open No. 2000-151509.

In this configuration, an electric circuit configured to generate a signal for reduction of noise by inverting an original signal is provided, and then the original signal and the signal for reduction of noise are transmitted independently by two light sources.

These signals are converted independently to electric signals on the receiving side, and then noise is reduced by acquiring a difference between these electric signals.

The related art as described above and the acoustic signal receiving apparatus of the embodiment disclosed here in which the FPI-PAT system of this disclosure is applied are basically different from each other in the following points.

In other words, with the FPI-PAT system of the acoustic signal receiving apparatus of the embodiment disclosed here, a signal to be detected does not exist as an electric signal in advance, and is generated by converting an acoustic wave directly to a light intensity signal of the probe light.

Therefore, it is difficult that a process of receiving the acoustic wave signal in some form, providing a unit having a function to generate a signal reduction of on the basis of the received signal, and generating the signal for reduction of noise by using the unit is provided at some position during the conversion process.

In addition to noise ridden on the probe light after the signal for reduction of noise has formed, in the case of the FPI-PAT, noise caused by mechanical fluctuations of the optical system or light from the outside is also ridden even while the probe light from the light source reaches the FPI-PAT.

Therefore, noise of the light intensity generated in entire part of an optical path of light from the light source until the light is converted into electricity needs to be reduced as a whole not only after formation of the signal for reduction of noise like in the related art, but also in previous phase.

In this case, in the embodiment disclosed here, even when noise is generated before entering the FPI-PAT, a signal of a photo-acoustic wave is ridden on the probe light by multiplexing the probe light generated by the light intensity change by reflectivity change at the FPI sensor.

When the probe light is subject to the intensity modulation at the FPI sensor as described above, the signal for reduction of noise generated directly at the FPI sensor is converted into an electric signal automatically and then the above-described process is performed. Accordingly, noise reduction including the light intensity change generated before entry to the FPI-PAT is achieved.

Exemplary Embodiments

Exemplary Embodiments of this disclosure will be described below.

Exemplary Embodiment 1

As Exemplary Embodiment 1, an example of a configuration of a photo-acoustic tomography provided with an acoustic signal receiving apparatus on the basis of the FPI-PAT system will be described with reference to FIG. 1.

Figure 1:
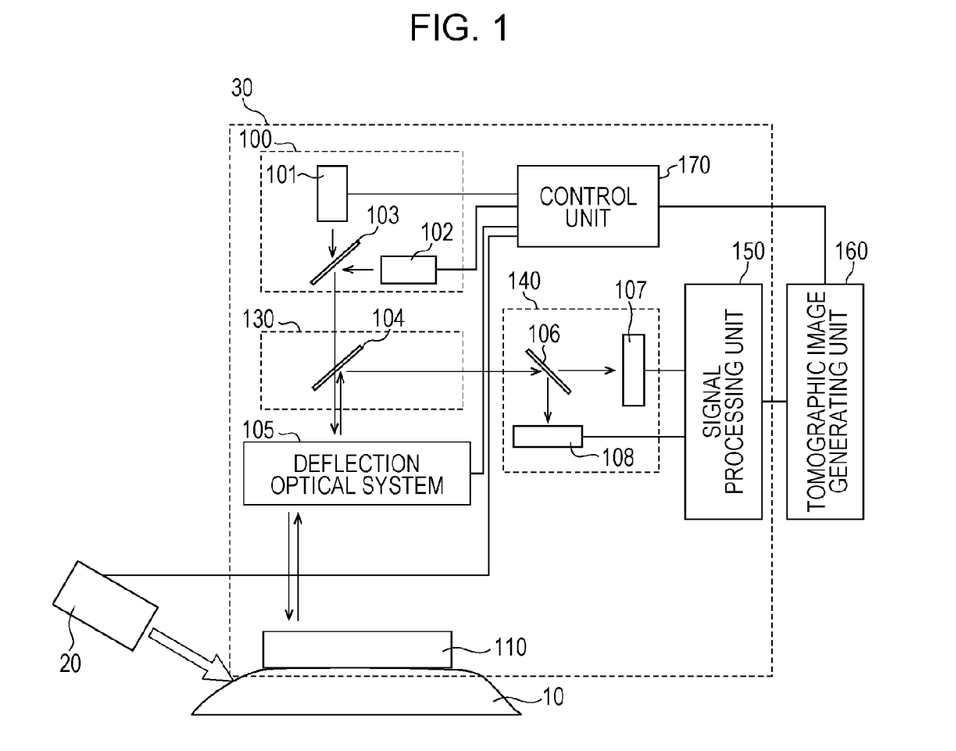
FIG. 1 is an explanatory drawing illustrating an example of a configuration of a photo-acoustic tomography provided with an acoustic signal receiving apparatus of Exemplary Embodiment 1 of this disclosure.

The photo-acoustic tomography provided with the acoustic signal receiving apparatus of Exemplary Embodiment 1 includes a light irradiating unit (photo-acoustic generating light source) 20 configured to irradiate a measurement object 10 with light that generates a photo-acoustic wave, an acoustic wave acquiring unit (acoustic signal receiving apparatus) 30 configured to acquire an acoustic wave signal from which noise caused by an intensity change of light generated by a factor other than the photo-acoustic wave signal is reduced, and a tomographic image generating unit 160 configured to generate a 3D tomographic image by the acoustic wave signal from which noise from the acoustic wave acquiring unit 30 is reduced as illustrated in FIG. 1.

Subsequently, a configuration of the acoustic wave acquiring unit (acoustic signal receiving apparatus) 30 of Exemplary Embodiment will be described further in detail.

The acoustic wave acquiring unit 30 includes a probe light generating section 100 configured to generate two rays of light having wavelengths different from each other and put these rays of light together on a single optical path, and a deflection optical system 105 configured to focus a beam generated by the probe light generating section to a desired position of the FPI.

The acoustic wave acquiring unit 30 also includes an FPI sensor 110 configured to focus the probe light emitted from the deflection optical system and modulate the acoustic wave signal from the measurement object 10 into a light intensity, and a reflecting light separating section 130 configured to separate light returned by being reflected from the FPI sensor from incident light.

The acoustic wave acquiring unit 30 further includes a detecting unit 140 configured to separate the reflected light separated by the reflecting light separating section 130 on the basis of the wavelength and acquire light intensity signals of the respective wavelengths, a signal processing unit 150 configured to obtain a difference between the signals obtained by the detecting unit 140, and a control unit 170 configured to control the movement of each structure of the apparatus.

The photo-acoustic tomography of Exemplary Embodiment is configured to generate an image as a 3D tomographic image by the tomographic image generating unit 160 by using the acoustic wave signal synthesized and having noise reduced therefrom at the signal processing unit.

Hereinafter, a flow until the 3D tomographic image is acquired by using the acoustic wave signal acquired by the acoustic wave acquiring unit 30 including detailed configurations of the respective portions will be described.

First of all, the probe light generating section 100 will be described.

The probe light generating section 100 includes a LD 101 and a LD 102, which are DFB semiconductor lasers from which a laser of a 780 nm band is emitted, and a half mirror 103 having a reflectivity of 50% for superimposing rays of light emitted therefrom with the same optical path.

The wavelengths of the rays of light emitted from the LD 101 and the LD 102 are adapted to two wavelengths at which the amounts of change (differential value) of wavelength dependency of reflectivity (reflectivity spectrum) of the FPI sensor 110 are maximized and the signs become opposite as described above.

Specifically, the reflectivity of the FPI sensor is as illustrated in FIG. 6, in which the LD 101 is 782.21 nm, the LD 102 is 788.48 nm.

The rays of light emitted from the LD 101 and the LD 102 pass through the half mirror 103, are synthesized on the same optical path, and are output as one beam in which two beams advance along paths spatially close to each other in the extreme.

The beam output from the probe light generating section 100 is deflected by the deflection optical system 105 that has a function to deflect and focus the beam on the FPI sensor.

The deflection optical system 105 has a configuration in which the direction of deflection can be changed, and is moved by a signal from the control unit 170.

The deflection optical system 105 which is used here may be a configuration used in the related art including an optical system used in "Backward-mode multiwavelength photo acoustic scanner using a planer Fabry-Perot polymer film ultrasound sensor for high-resolution three-dimensional imaging of biological tissue, Applied Optics, 47, 4. (2008)".

The light emitted from the deflection optical system 105 is focused to a desired position on the FPI sensor 110. The focused light changes in intensity independently and is reflected according to the reflectivity at each respective wavelengths of the FPI sensor.

As described above, when the acoustic wave signal from the measurement object 10 enters, increase and decrease in reflectivity of the two rays of probe light at the respective wavelengths change in the opposite directions. Accordingly, the irradiated light modulates the acoustic wave signal from the measurement object into the light intensity signal without the intermediary of a signal for reduction of noise generating unit such as an electric circuit or the like and, simultaneously, the rays of probe light are directly formed into the signals for reduction of noise automatically.

The rays of probe light modulated in intensity by the FPI sensor 110 and reflected advance on the optical path of the light incident on the FPI sensor 110 in the opposite direction.

Specifically, the reflected light passes through the deflection optical system 105 again, and advances to the reflecting light separating section 130.

The reflected light is separated from the optical path of the incident light by the reflecting light separating section 130. The reflecting light separating section 130 is separated from the optical path of the incident light by a half mirror 104 having a reflectivity of 50%. The separated light enters the detecting unit 140 configured to detect the intensity.

The detecting unit 140 includes a wavelength filter 106, and the two rays of probe light having different wavelengths are separated by the wavelength filter 106 into respective wavelength components.

The rays of light having the respective wavelengths enter a PD 107 and a PD 108, and light intensity signals of the respective wavelengths are converted into electric signals. The wavelength filter 106 used here is a filter generally referred to as a band-pass filter.

In this Exemplary Embodiment, the band-pass filter configured to transmit light having a 10 nm range of wavelength from 785 nm to 795 nm and reflect wavelength in the periphery thereof is used.

In this Exemplary Embodiment, positions having different reflectivity inclinations of the FPI sensor 110 in the same dip are not used, and different dips are used for providing the two rays of probe light with a large wavelength difference of 5 nm or more.

These wavelengths setting is based on the fact that a dip wavelength varies depending on the temperature and the irradiation spot of the FPI sensor 110.

Specifically, these wavelengths setting is based on the necessity of an adequate margin in design which prevents probe light to be transmitted and probe light to be reflected from resulting in unintended transmission or reflection at the band-pass filter 106 even when a laser wavelength follows the movement of the dip.

A light source used in this Exemplary Embodiment has the same design, and is a light source including two semiconductor chips having different oscillation wavelengths due to individual difference between elements.

Therefore, a wavelength difference on the order of 5 nm is a realistic value.

In contrast, when taking priority of easiness of manufacture of the band-pass filter, the wavelength difference is preferably 10 nm or more. Therefore, when usage of the element having different design is allowed, a wavelength difference is preferably 10 nm or more.

One of the electrical signals obtained by the detecting unit 140 is inverted by the signal processing unit 150, and then, both signals are added. In other words, the signal processing unit 150 acquires a difference between the two electric signals corresponding to the respective wavelengths.

Accordingly, acoustic wave signal components are emphasized, noises thereof are annihilated each other and, consequently, noise is suppressed in total. Consequently, the signals with less noise are obtained.

The process of generating a difference between the signals at the signal processing unit 150 may be performed by an electric circuit which is the same as that used in Japanese Patent Laid-Open No. 2000-151509.

The acoustic wave signal in which noise is alleviated by the signal processing unit 150 is input to the tomographic image generating unit 160, whereby the acoustic wave signal for generating the image is memorized.

According to a series of flow described above (from generation of the probe light by the probe light generating section 100 to the memorization of the acoustic wave signal by the tomographic image generating unit 160), acquisition of the acoustic wave signal at one point in a plane of the FPI sensor 110 is completed.

Acquisition of a plurality of the acoustic wave signals on the FPI sensor 110 is needed for generating a tomographic image.

Therefore, the entire part is controlled by the control unit 170 to acquire the acoustic wave signal at a plurality of positions on the FPI sensor 110.

Specifically, the control unit 170 firstly moves the deflection optical system 105 to a desired position. Subsequently, the control unit 170 generates a laser beam for generating the photo-acoustic wave and causes the probe light generating section 100 to generate probe light.

The control unit 170 causes the tomographic image generating unit 160 to memorize waveforms of the photo-acoustic wave signal acquired by the series of flow and the positions on the FPI sensor 110 at that time independently for each positions on the FPI sensor 110.

The control unit 170 repeats this process to acquire all the acoustic wave signals at the required positions on the FPI sensor 110 and memorizes the same in the tomographic image generating unit.

Finally, when all items of information are acquired, a 3D tomographic image is calculated by the tomographic image generating unit 160, so that the intended 3D tomographic image is obtained.

In this Exemplary Embodiment, the DFB laser is employed as the laser light source in the probe light generating section 100. However, the laser light source is not limited to the DFB laser as long as the laser has a single wavelength spectrum. For example, a VCSEL is also applicable. Although the wavelength band of the laser in this Exemplary Embodiment is 780 nm, the invention is not limited thereto. For example, a 850 nm band, a 980 nm band, and 1.55 μm band may also be applicable.

Although the two beams are combined by using the half mirror in the probe light generating section 100, the two beams may be combined by using a light waveguide or the like.

Although the half mirror is employed as the reflecting light separating section 130, the reflecting light separating section 130 may be replaced by a combination of a polarization beam splitter and a reflection plate as long as the direction of polarization of the two rays of probe light are aligned.

In this case, a 90 degrees shift between the direction of polarization of the ray of probe light incident on the FPI sensor 110 when passing through the reflecting light separating section 130 and the direction of polarization of the light reflected from the FPI sensor 110 incident on the reflecting light separating section 130 contributes to control of the transmission and the reflection of the beam at the polarization beam splitter.

Although the two rays of probe light having different wavelengths are employed in this Exemplary Embodiment, three or more rays of probe light may be employed as long as rays of probe light having wavelengths at which the signs of the differential values obtained by the FPI sensor 110 are different are included. In this case, since the values at the same moment are further averaged, an effect of reduction of noise component is increased.

In Exemplary Embodiment 1, the acoustic wave acquiring unit 30 that employs the FPI sensor uses the photo-acoustic wave signal for acquiring an acoustic signal for obtaining a 3D tomographic image. However, the usage of the photo-acoustic wave signal is not limited thereto, and may be applied for acquiring other acoustic signal. The same applies also to Exemplary Embodiment 2 to Exemplary Embodiment 5.

Exemplary Embodiment 2

Figure 2:
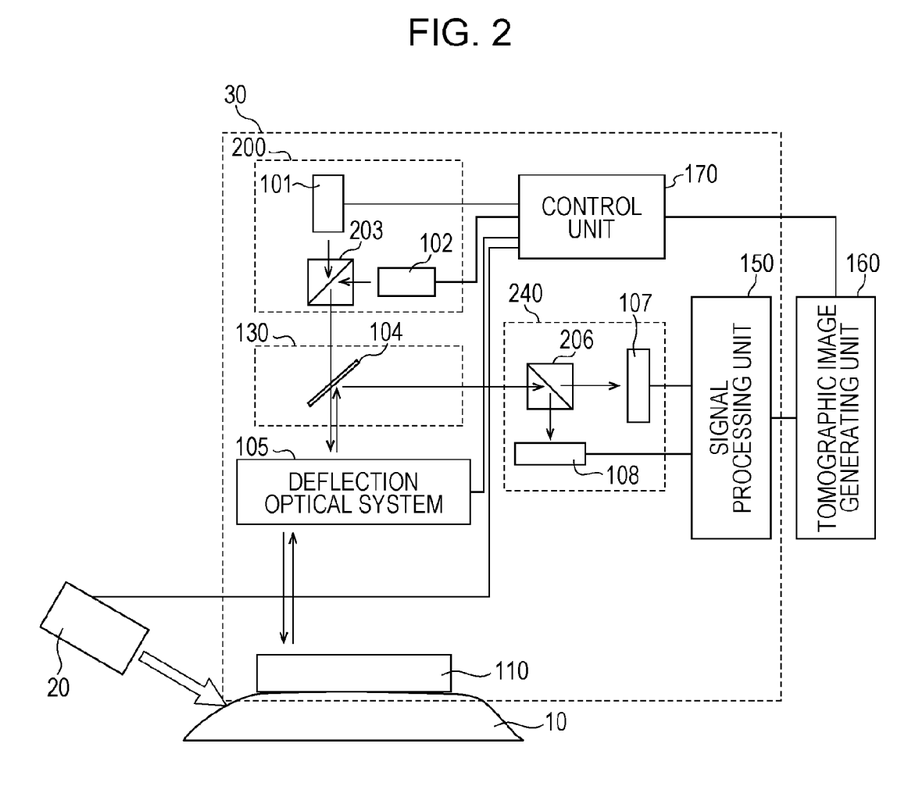
FIG. 2 is an explanatory drawing illustrating an example of a configuration of a photo-acoustic tomography provided with an acoustic signal receiving apparatus of Exemplary Embodiment 2 of this disclosure.

As Exemplary Embodiment 2, an example of a configuration of a photo-acoustic tomography provided with an acoustic signal receiving apparatus on the basis of an FPI-PAT system having different configuration from that in Exemplary Embodiment 1 will be described with reference to FIG. 2.

Different points between Exemplary Embodiment 1 and Exemplary Embodiment 2 is the configurations of a probe light generating section 200 and a detecting unit 240, and other points are basically the same. Therefore, the same numerals are assigned to the same members.

In Exemplary Embodiment 1, as the method of separating the two rays of light having different wavelengths by the detecting unit 140, the difference in wavelength is used, and the two rays of light are separated by allowing one of the rays of light to be transmitted and the other light to be reflected by the wavelength filter 106 having a wavelength selecting property.

In contrast, in the detecting unit 240 of Exemplary Embodiment 2, the directions of polarization of the two rays of light having different wavelengths are maintained to be different by 90 degrees. Therefore, as the method of separating the two rays of probe light, the difference in direction of polarization is used, and a member for changing the direction of advancement of light depending on polarization characteristics is used.

An advantage of using the difference in direction of polarization is in that separation is performed even though the wavelengths are close to each other as long as the directions of polarization are maintained.

In Exemplary Embodiment 1, since the separation is performed on the basis of the wavelength, sufficiently different wavelengths are used for performing the separation even when the wavelengths of the rays of probe light are changed due to a spatial distribution of the reflectivity dips of the FPI sensor or a change of the wavelength of the dip caused by the temperature variation.

In contrast, in Exemplary Embodiment 2, the wavelengths need not to be significantly different from each other.

Therefore, portions having respective inclinations of the same dip may be used, and the wavelengths are set in this manner in the following detailed disclosure as well.

The configurations of the Exemplary Embodiment 2 also have advantages that wavelength can be shifted following to the dip shift without consideration of the difference between wavelengths of probe lights and wavelength dependency characteristics of the wavelength filter.

A detailed configuration of Exemplary Embodiment 2 will be described.

The probe light generating section 200 includes the two DFB lasers 101 and 102.

The direction of polarization of the DFB laser 101 is determined so as to match the direction of transmission thereof through a polarization beam splitter 203.

In contrast, the polarization of the DFB laser 102 is fixed to a direction of reflection by the polarization beam splitter 203.

In this manner, rays of light having two wavelengths are multiplexed by the polarization beam splitter (wave multiplexer) 203, and are emitted from the probe light generating section 200 as a beam advancing on the same optical path.

The rays of probe light emitted from the probe light generating section 200 pass through the deflection optical system 105 composed of the same members as in Exemplary Embodiment 1, and are focused on the FPI sensor 110. The two rays of probe light are subject to modulation by which the intensities become opposite to each other and are reflected therefrom by the FPI sensor 110.

Subsequently, the rays of probe light pass through the deflection optical system 105 and the reflecting light separating section 130 composed of the same members as in Exemplary Embodiment 1, and enter the detecting unit 240. Since the same members as Exemplary Embodiment 1 have the same functions as those in Exemplary Embodiment 1, description will be omitted.

The detecting unit 240 includes a polarization beam splitter 206 configured to separate light depending on the polarization and two PDs 107 and 108 for monitoring the light intensities of the two rays of probe light independently.

The two rays of probe light here are separated by being set so as to have different directions of polarization. Therefore, there is no limit in the proximity of the wavelengths as described above.

The electric signals corresponding to the two lights separated by the polarization beam splitter 206 are subject to noise reduction in the signal processing unit 150 that has the same configuration as that in Exemplary Embodiment 1, and are memorized in the tomographic image generating unit 160. In the same manner as Exemplary Embodiment 1, the control unit 170 controls the entire part, acquires acoustic wave signals in a plane of the FPI sensor, and memorizes the acquired signals in the tomographic image generating unit 160. Finally, the tomographic image is generated to complete the procedure.

Exemplary Embodiment 3

Figure 3:
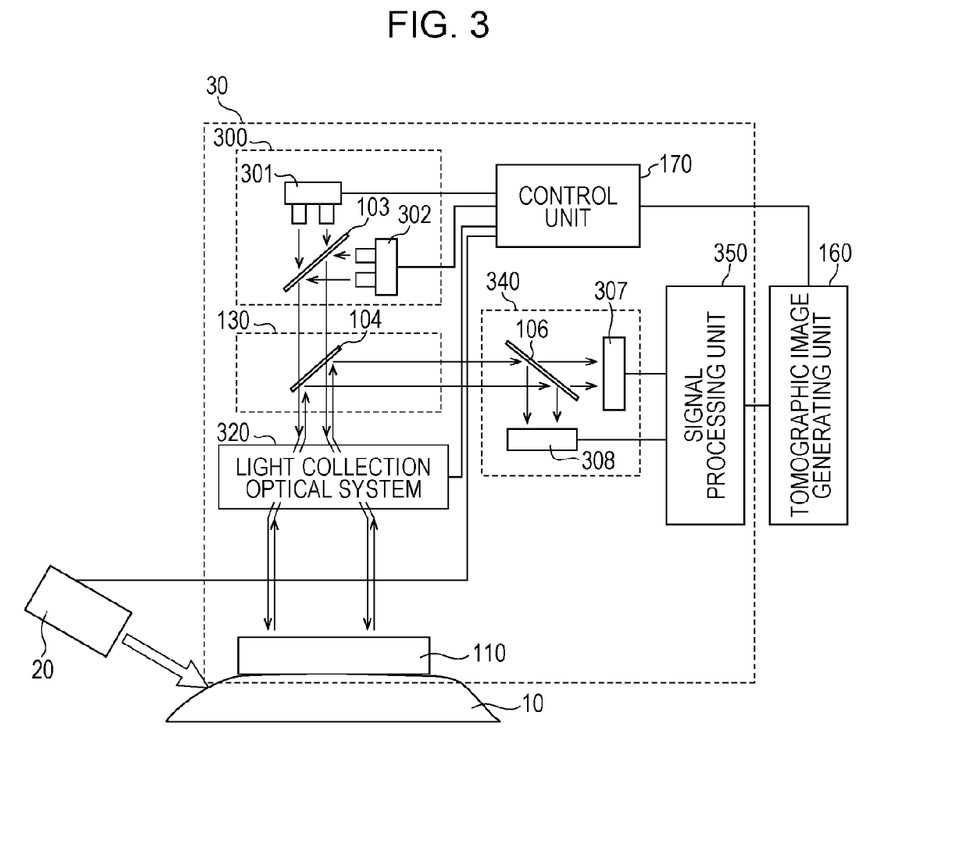
FIG. 3 is an explanatory drawing illustrating an example of a configuration of a photo-acoustic tomography provided with an acoustic signal receiving apparatus of Exemplary Embodiment 3 of this disclosure.

As Exemplary Embodiment 3, an example of a configuration of a photo-acoustic tomography provided with an acoustic signal receiving apparatus on the basis of a FPI-PAT system having different configuration from those in Exemplary Embodiments 1 and 2 will be described with reference to FIG. 3.

A different point between Exemplary Embodiment 3 and the Exemplary Embodiments 1 and 2 is that a method of acquiring the acoustic wave signals at a plurality of different positions in the plane of the FPI sensor is different, and other configurations are basically the same. Therefore, the same numerals are assigned to the same members.

In Exemplary Embodiment 1 and Exemplary Embodiment 2, a single beam is moved to various positions by using the optical system configured to polarize the beam to receive the photo-acoustic wave signal.

In contrast, in Exemplary Embodiment 3, a laser array light source configured to emit a plurality of beams simultaneously in parallel to each other is used, and one of light-emitting points on a laser array corresponds to a specific position on the FPI sensor.

In other words, the light-emitting points on the array and the positions on the FPI sensor are in one-to-one correspondence, and the position on the FPI sensor from which the photo-acoustic wave is to be acquired automatically is determined by selecting a light source that electrically emits light from a plurality of the light sources existing in the array.

Furthermore, in the case of the laser array, the laser beams may be emitted simultaneously, and are focused on different points on the FPI sensor.

Therefore, when the laser array is caused to emit beams simultaneously, the change of the light intensity by using the photo-acoustic waves at respective positions on the FPI sensor may be performed independently and simultaneously at the respective positions.

A detailed configuration of Exemplary Embodiment 3 will be described focusing on the point different from Exemplary Embodiment 1 and Exemplary Embodiment 2.

A probe light generating section 300 includes a VCSEL array (first array light source) 301 and a VCSEL array (second array light source) 302 of a 780 nm band arranged in 10×10 pattern, and the half mirror 103 configured to multiplex rays of light therefrom.

The wavelengths of the VCSEL arrays 301 and 302 are the same as those of the LD 101 and the LD 102 of Exemplary Embodiment 1. The FPI sensor 110 is formed of the same member as Exemplary Embodiment 1, and hence a relationship between the wavelengths of the two light sources and the reflectivity spectrum of the FPI sensor 110 is also the same.

Rays of light emitted from the probe light generating section 300 are focused on the FPI sensor 110 from on light emitting point to another of the VCSEL array by a light focusing optical system 320. The light focusing optical system 320 is a telecentric optical system.

Two rays of probe light having different wavelengths from the VCSEL array 301 and the VCSEL array 302 are focused on respective spatial positions in the plane of the FPI sensor 110, and as described in the Exemplary Embodiment 1, the respective wavelengths have the relationship with respect to the reflectivity spectrum of the FPI sensor 110. Therefore, when the light intensities are modulated by the photo-acoustic wave, the light intensities are modulated to be opposite to each other.

The rays of probe light reflected from the FPI sensor 110 are separated from the rays of probe light incident on the FPI sensor 110 by the half mirror 104 and enter a detecting unit 340.

The detecting unit 340 includes the wavelength filter 106 and CCD sensors 307 and 308. The wavelength filter 106 allows the probe light to be transmitted therethrough or reflected depending on the difference in wavelength as in Exemplary Embodiment 1.

The rays of probe light are focused respectively on the CCD sensors 307 and 308.

The rays of probe light are focused on the CCDs in the same array as the light emission from the VCSEL arrays.

Therefore, by monitoring the intensity change with time from one focusing point to another with the CCD sensors, a waveform of the acoustic wave signal within the plane of the FPI sensor 110 may be obtained as an electric signal.

The obtained electric signals are subject to the same process as in Exemplary Embodiment 1 by a signal processing unit 350, and the noise is reduced. In Exemplary Embodiment 3, since the waveforms of the intensity changes of the two rays of probe light are sent in the form of digital signals from the detecting unit 340, the signal processing unit 350 has a function to perform generation of a difference between the digital signals.

Subsequently, the signal is transmitted to the tomographic image generating unit 160, where calculation of the 3D tomographic image is performed, so that a 3D tomographic image is obtained.

In Exemplary Embodiment 3, the detecting unit 340 detects the change of the light intensity of the respective light-emitting points by using the CCDs. However, the light intensity changes of the respective light-emitting points may be converted into the electric signals by using an array of a plurality of PDs arranged in a plane and aligning the respective PDs and the focused light-emitting points.

Exemplary Embodiment 4

Figure 4:
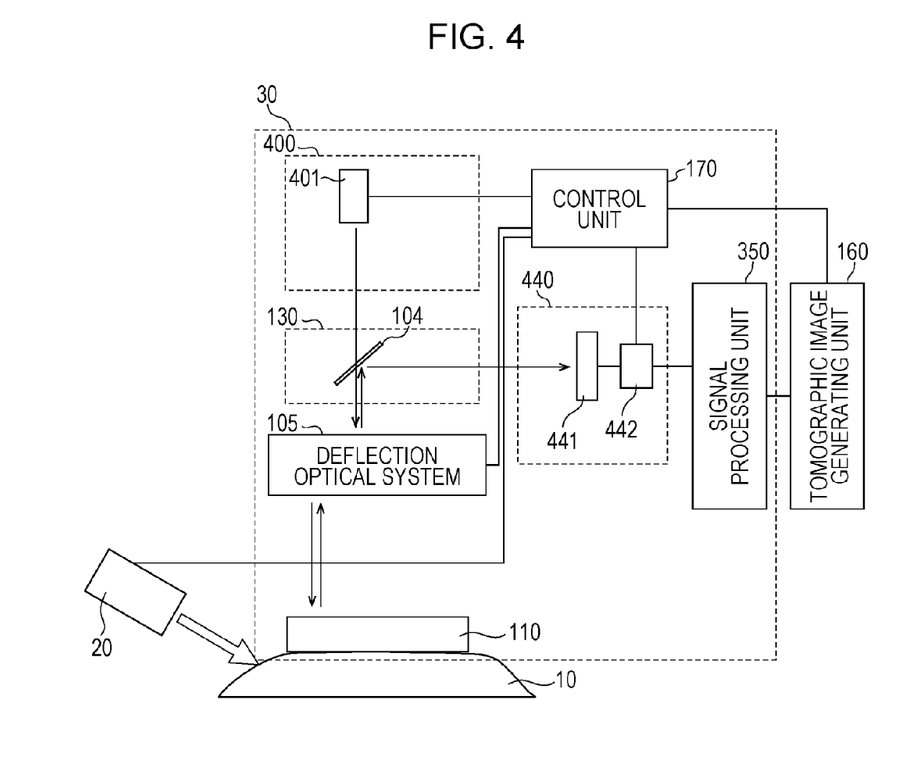
FIG. 4 is an explanatory drawing illustrating an example of a configuration of a photo-acoustic tomography provided with an acoustic signal receiving apparatus of Exemplary Embodiment 4 of this disclosure.

As Exemplary Embodiment 4, an example of a configuration of a photo-acoustic tomography provided with an acoustic signal receiving apparatus on the basis of an FPI-PAT system having different configuration from those in Exemplary Embodiments 1 to 3 will be described with reference to FIG. 4.

A different point between Exemplary Embodiment 4 and Exemplary Embodiment 1 to Exemplary Embodiment 3 is the following point, and other points are basically the same. Therefore, the same numerals are assigned to the same members.

In Exemplary Embodiment 1 to Exemplary Embodiment 3, the two rays of probe light having different wavelengths are generated by the different light sources. Then, the rays of light are multiplexed and branched, and the light is converted to the electric signal.

In contrast, in Exemplary Embodiment 4, the wavelength of the light emitted from the probe light generating section is changed step by step to predetermined two or more different wavelengths at a certain time interval.

In addition, in the light-receiving side, a signal is acquired synchronously with the steps and divided by time, and then data of the respective wavelengths are connected to each other, whereby the modulated waveform of the light intensity by the FPI sensor at the two different wavelengths are obtained.

The characteristic of Exemplary Embodiment 4 is that the number of components of the light source, a light receiving sensor, and the optical system is reduced.

For example, when a wavelength-variable light source that is capable of changing the wavelength to a high speed is employed as a light source, the number of light sources is reduced, and a member configured to multiplex the waves is no longer necessary. In addition, alignment of optical axes at the time of multiplexing the waves is no longer necessary. Also, on the light-receiving side, the number of members for branching the wave and the light receiving sensors may be reduced.

A detailed configuration of Exemplary Embodiment 4 will be described.

A probe light generating section 400 is composed of a wavelength-variable SSG-DBR laser 401. The SSG-DBR laser changes the wavelengths at every 10 ns between two levels, 782.2 nm and 788.4 nm, which are the wavelengths of the two rays of probe light in Exemplary Embodiments.

The characteristics of the laser required in Exemplary Embodiment 4 will be considered. As regards switching speed between the wavelengths, the speed of switching between the two wavelengths is required to be as fast as several nanoseconds. Therefore, wavelength control by using a change of the refractive index by injecting carrier or applying an inverted bias voltage is desirable in comparison with usage of a reflectivity change by heat.

In contrast, stability of the wavelength is required only during a light-emitting period. Specifically, the wavelength needs only to be stable during the above-described 10 ns. Therefore, the stability of the wavelength between the two wavelengths is not required for a longer time.

Light emitted from the probe light generating section 400 passes through the deflection optical system 105, and focused on a predetermined position on the FPI sensor 110. At this time, the modulation is performed by using a reflectivity spectrum of the FPI sensor 110 with influence from the photo-acoustic wave at the same timing as the wavelengths of several timings.

The probe light modulated and reflected by the FPI sensor 110 is taken out by the deflection optical system 105 and the reflecting light separating section 130, and enters a detecting unit 440.

The detecting unit 440 includes one photo detector 441 and a signal regenerating unit 442 as a reflectivity change acquiring unit. The photo detector 441 acquires a temporal waveform of incident light.

The signal regenerating unit 442 separates the light into two wavelengths each on the basis of the temporal waveform from the photo detector 441 and information of time axis of the light-emitting wavelength fed from the light source.

Furthermore, the signal regenerating unit 442 performs calculation for recreating the two each waveforms from discrete information. Accordingly, the inverted signal which is the same as those in Exemplary Embodiments 1 to 3 is obtained.

Subsequently, the obtained electrical signals are subject to the same noise reduction process as in Exemplary Embodiment 3 by the signal processing unit 350, and are sent to the tomographic image generating unit 160. Then, in the same manner as Exemplary Embodiments 1 and 2, under the control of the control unit 170, acoustic wave signals are acquired at required positions in a plane of the FPI sensor 110 and finally, the tomographic image is generated to end the procedure.

The interval of switching of the two wavelengths needs to be two times or more shorter than a frequency component of photo-acoustic wave frequency or noise frequency since the waveform is re-created from the discrete information.

In Exemplary Embodiment 4, the photo-acoustic wave needs to acquire a component on the order of 10 MHz, and mechanical fluctuation of the optical system has a frequency component of 1 MHz or lower. Therefore, two times or more of a high-frequency photo-acoustic wave, that is, 20 MHz or more needs to be secured. Accordingly, in Exemplary Embodiment 4, acquisition is performed every 10 ns, that is, at 100 MHz, which is ten times the frequency of the photo-acoustic wave.

In Exemplary Embodiment 4, the SSG-DBR laser is used as a laser that changes the wavelength at a high speed. However, this disclosure is not limited thereto.

A probe light generating section 400 configured to multiplex lasers having two different wavelengths and causes one by one to be illuminated at a certain intervals (by elapse of time) also provides the same advantages, although the number of components is increased.

Exemplary Embodiment 5

As Exemplary Embodiment 5, an example of a configuration different from those in Exemplary Embodiments 1 to 4 will be described.

A point different from each other between Exemplary Embodiment 5 and Exemplary Embodiments 1 to 4 is as follows.

Exemplary Embodiment 5 has the same basic configuration as Exemplary Embodiment 1 to Exemplary Embodiment 4. However, setting of the wavelength of one of the two rays of probe light is different.

In Exemplary Embodiment 1 to Exemplary Embodiment 4, the wavelength is set so that the light intensity is modulated when the photo-acoustic wave enters the FPI sensor 110. In contrast, in Exemplary Embodiment 5, the wavelength of one of the rays of probe light is set to a wavelength at which the light intensity is not subject to modulation by the FPI sensor 110. In other words, the wavelength of one of the rays of probe light is set based on reflectivity spectrum of the FPI sensor 110 so that a differential value of reflectivity spectrum of the FPI sensor 110 is zero or close to zero.

With this setting, the probe light which is not subject to the intensity modulation by the FPI sensor 110 is subject to the modulation of light intensity only with the noise generated in a range from the light source to the detecting unit.

An advantage of setting the wavelength in this manner in Exemplary Embodiment 5 is that accuracy required for adjusting the wavelength may be suppressed to a low level.

The wavelength dip of the reflectivity of the FPI sensor 110 is as narrow as 0.3 nm, or even narrower, so that adjustment with accuracy is needed by the unit of accuracy not larger than the corresponding wavelength in order to receive the intensity modulation by the photo-acoustic wave.

Therefore, in order to modulate the intensities of the both two rays of probe light, adjustment of the wavelength at the above-described accuracy needs to be performed on the both two rays of probe light. More specifically, the wavelength of the laser is gradually changed and, accordingly, a change in intensity at the detecting unit that converts the light intensity into the electric signal is measured, and data of the wavelength dependency of the reflectivity as illustrated in FIG. 6 is obtained therefrom. Then, an adjustment that a wavelength at which the differential value becomes a maximum value is determined from the data is necessary. The control is performed by the control unit 170 controlling the entire procedure.

In contrast, in Exemplary Embodiment 5, since one of the rays of probe light has a wavelength at a position that is not subject to the modulation of light intensity, preferably, near the middle of two resonance dips in the reflectivity spectrum of the FPI sensor, the accuracy required for adjusting the wavelength may be lowered.

Another advantage of Exemplary Embodiment 5 is that no deterioration of the signal occurs due to cross talk. When cross talk occurs in the light intensity of the two rays of probe light, the signal component of the photo-acoustic wave works in a compensating direction in the case of the inverted signal.

In contrast, in Exemplary Embodiment 5, since an AC component exist little on the side that is not subject to the modulation of light intensity if there is no noise, the AC component, that is, it is difficult to compensate the component of the acoustic wave signal even though cross talk occurs.

Figure 5:
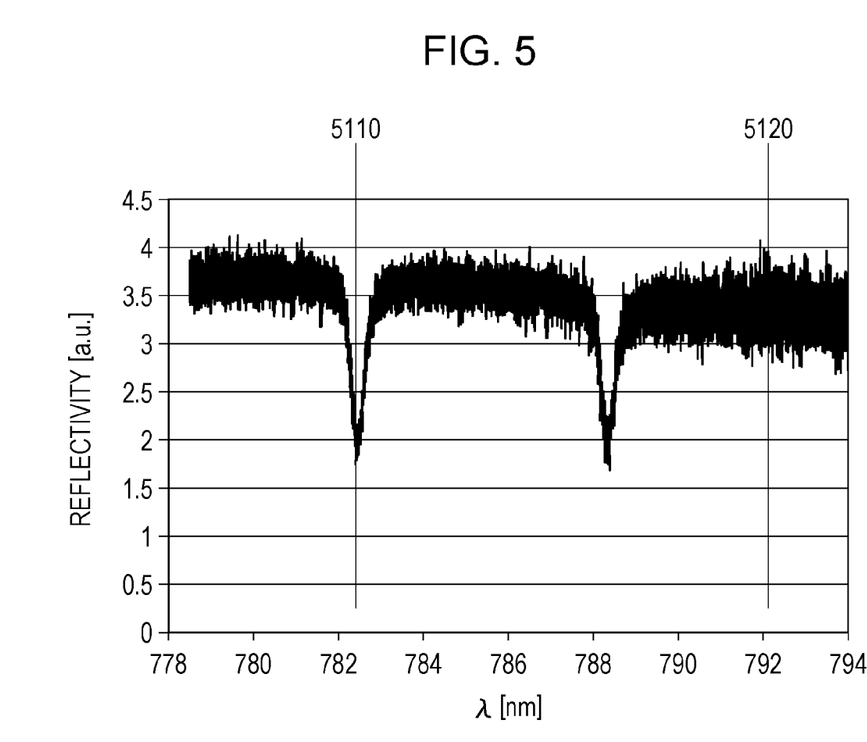
FIG. 5 is an explanatory drawing illustrating an example of wavelength setting by a photo-acoustic tomography provided with an acoustic signal receiving apparatus of Exemplary Embodiment 5 of this disclosure.

Referring now to FIG. 5, an example of setting of the wavelength in Exemplary Embodiment 5 will be described.

In this manner, the first wavelength is set to 782.2 nm, and the second wavelength is set to 792 nm.

Since the second wavelength is set to a position having low wavelength dependency in the reflectivity spectrum of the FPI sensor, even when the photo-acoustic wave enters the FPI sensor, the intensity modulation caused thereby is sufficiently small in comparison with the first wavelength. For example, the differential value of the reflectivity spectrum of the Fabry-Perot sensor in the first and second wavelengths may be set to have 10 times or more difference.

In Exemplary Embodiment 5, in the same manner as Exemplary Embodiment 1, the wavelength difference that allows sufficient wavelength separation by the wavelength filter is preferably secured.

Since the separation of the wavelength is performed under the same principle as in Exemplary Embodiment 1, preferable conditions are the same as in Exemplary Embodiment 1.

Since the configuration of the apparatus other than the setting of the wavelength as described above is the same as in Exemplary Embodiment 1, description will be omitted. In Exemplary Embodiment 5, the wavelength of one of the rays of probe light is set to a position that is not subject to the intensity modulation by the FPI sensor in the configuration of Exemplary Embodiment 1. By performing the same setting of the wavelength in the configurations from Exemplary Embodiments 2 to 4, the same advantages as Exemplary Embodiment 5 will be achieved.

In view of Exemplary Embodiments 1 to 5 totally, a concept of this disclosure is that the rays of probe light are set to have two wavelengths having different differential values of the reflectivity spectrum of the Fabry-Perot sensor. The concept of this disclosure is reduction of noise based on the difference between two signals having different ratio between the signal component and the noise component generated automatically by the Fabry-Perot sensor.

In Exemplary Embodiment 1 to Exemplary Embodiment 4, the wavelengths of the two rays of probe light are set as preferable conditions when putting a high priority on increasing the difference between the components of the acoustic wave signals of the two signals, that is, increasing the magnitude of the signal component when the process of reducing the noise is performed. In contrast, in Exemplary Embodiment 5, the wavelengths of the rays of probe light are set under preferable conditions by putting a high priority on alleviation of a load of a process for compensating displacement of the dip position of the Fabry-Perot sensor caused by the change of the environment temperature. Specifically, a condition which provides a stable signal without performing precise correction of the wavelength of one of the rays of probe light is achieved.

However, the set value of the wavelength is not limited thereto, and what is essential is that the wavelengths of the two rays of probe light have a difference as described above. Therefore, what is essential is that the wavelength of the first probe light on which the signal component rides is set to a wavelength which is close to a wavelength at which the differential value of the reflectivity spectrum becomes the maximum or the minimum value (the maximum value in absolute value in both cases), and the wavelength of the other probe light is set to the second wavelength different therefrom. However, when the relationship between the dip and the wavelengths of the rays of probe light are displaced due to the temperature change and hence the wavelength of the probe light is displaced so that the sign of the differential value goes to the opposite side with respect to the dip, the ratio including the signal and the sign of the noise components is abruptly changed, and hence the noise reducing cannot be performed effectively under the assumed signal processing conditions. In addition, since the difference does not appear when the differential value of the second wavelength becomes the same as the first wavelength due to the temperature change, no advantage is achieved. Therefore, the set wavelength of the second probe light is preferably set away from the first wavelength and also away from the position of the wavelength of the dip in prospect of the amount of change of the wavelength due to the temperature change so that the precise correction of the wavelength of the second probe light do not have to be performed.

As regards the differential value with respect to the first wavelengths, from the characteristic that the reflectivity of the Fabry-Perot sensor changes cyclically, it is necessary to set so that the same differential value exists not only in the wavelength which is the same as the wavelength as the first wavelength and also in the wavelength shifted by one cycle or more, and overlapping therewith is avoided. The same applies to the dips because the dips exist also cyclically. The above described relationship is expressed by an expression given below. (In the case where the first wavelength is set to a value close to the maximum value of the differential value of the reflectivity spectrum)

$$\lambda_1 + \Delta\lambda \cdot \Delta t \leq \lambda_0 \leq \lambda_2 - \Delta\lambda \cdot \Delta t$$

Here, in the reflectivity spectrum between the first dip and the second dip adjacent to the first dip and having a wavelength larger than a wavelength corresponding to the first dip, $\lambda_0$ is the second wavelength, $\lambda_1$ is a wavelength at which the differential value of the reflectivity spectrum of the Fabry-Perot sensor that exists in the first dip becomes the maximum value, $\lambda_2$ is a wavelength corresponding to the second dip, $\Delta\lambda$ is a relative amount of change of the wavelengths of the light source and the reflectivity dip under an environmental temperature change per unit temperature, and $\Delta t$ is a change of the estimated environmental temperature.
(In the case where the first wavelength is set to a value close to the minimum value of the differential value of the reflectivity spectrum)

$$\lambda_3 + \Delta\lambda \cdot \Delta t \leq \lambda_0 \leq \lambda_4 - \Delta\lambda \cdot \Delta t$$

Here, in the reflectivity spectrum between the first dip and the second dip adjacent to the first dip and having a wavelength larger than a wavelength corresponding to the first dip, $\lambda_0$ is the second wavelength, $\lambda_3$ is a wavelength corresponding to the first dip, $\lambda_4$ is a wavelength at which the differential value of the reflectivity spectrum of the Fabry-Perot sensor that exists in the second dip becomes the minimum value, $\Delta\lambda$ is a relative amount of change of the wavelengths of the light source and the reflectivity dip under an environmental temperature change per unit temperature, and $\Delta t$ is a change of the estimated environmental temperature.

In any Exemplary Embodiments, reception of the photoacoustic wave has been described. However, the acoustic signal receiving apparatus according to this disclosure may be applied to the reception of any acoustic waves. For example, the acoustic signal receiving apparatus according to this disclosure may be applied to the reception of an echo generating by reflection of the transmitted acoustic wave in the measurement object.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-044271 filed Mar. 6, 2013, which is hereby incorporated by reference herein in its entirety.

What is claimed is:

1. An acoustic signal receiving apparatus comprising:
a Fabry-Perot sensor including a Fabry-Perot interferometer configured to convert an acoustic wave generated from a measurement object to a light intensity signal;
a first light source configured to emit light having a first wavelength, wherein the first wavelength is settable;
a second light source configured to emit light having a second wavelength different from the first wavelength, wherein the second wavelength is settable;
a detector configured to convert the light intensities of reflected rays of light obtained by irradiation of the Fabry-Perot sensor with rays of light from the first light source and the second light source into electric signals independently by the first wavelength and the second wavelength; and
a processor configured to acquire a difference between an electric signal corresponding to the first wavelength and an electric signal corresponding to the second wavelength,
wherein the first wavelength and the second wavelength are set so that differential values of reflectivity spectrum of the Fabry-Perot sensor are different at the first wavelength and the second wavelength.

2. The acoustic signal receiving apparatus according to claim 1, wherein the first wavelength and the second wavelength are such that signs of the differential values of the reflectivity spectrum of the Fabry-Perot sensor are opposite at the first wavelength and the second wavelength.

3. The acoustic signal receiving apparatus according to claim 1, wherein the first wavelength at which the differential value of the reflectivity spectrum of the Fabry-Perot sensor becomes a value close to the maximum value and wherein the second wavelength $\lambda_0$ falls within a range of the following expression;

$$\lambda_1 + \Delta\lambda \cdot \Delta t \leq \lambda_0 \leq \lambda_2 - \Delta\lambda \cdot \Delta t$$

wherein the reflectivity spectrum between a first dip and a second dip adjacent to the first dip and having a wavelength larger than a wavelength corresponding to the first dip, $\lambda_1$ is a wavelength at which the differential value of the reflectivity spectrum of the Fabry-Perot sensor becomes the maximum value, $\lambda_2$ is a wavelength corresponding to the second dip, $\Delta t$ is a change of an estimated environmental temperature, and $\Delta\lambda$ is a relative amount of change of the wavelength between the light source and the wavelength of a reflectivity dip per unit temperature.

4. The acoustic signal receiving apparatus according to claim 1, wherein the first wavelength at which the differential value of the reflectivity spectrum of the Fabry-Perot sensor becomes a value close to the minimum value and wherein the second wavelength $\lambda_0$ falls within a range of the following expression;

$$\lambda_3 + \Delta\lambda \cdot \Delta t \leq \lambda_0 \leq \lambda_4 - \Delta\lambda \cdot \Delta t$$

in the reflectivity spectrum between the first dip and the second dip adjacent to the first dip and having a wavelength larger than the wavelength corresponding to the first dip, $\lambda_3$ is a wavelength corresponding to the first dip, $\lambda_4$ is a wavelength at which the reflectivity spectrum of the Fabry-Perot sensor becomes the minimum value, $\Delta t$ is a change of an estimated environmental temperature, and $\Delta\lambda$ is a relative amount of change of the wavelength between the light source and the wavelength of the reflectivity dip per unit temperature.

5. The acoustic signal receiving apparatus according to claim 1, wherein the first light source and the second light source include different light sources.

6. The acoustic signal receiving apparatus according to claim 1, wherein the first light source and the second light source include a single light source configured to emit a plurality of wavelengths including the first wavelength and the second wavelength.

7. The acoustic signal receiving apparatus according to claim 6, wherein the single light source is configured to emit light having the first wavelength and light having the second wavelength alternately by elapse of time; and the processor acquires a difference between an intensity signal of a reflectivity change at the first wavelength and an intensity signal of a reflectivity change in the second wavelength on the basis of the electric signal and information on a temporary change of the wavelength of the single light source.

8. The acoustic signal receiving apparatus according to claim 7, wherein the reflectivity change between the first wavelength and the second wavelength is acquired on the basis of the electric signal and information on a temporary change of the wavelength of the single light source.

9. The acoustic signal receiving apparatus according to claim 1, further comprising an optical unit configured to synthesize rays of light from the first and the second light sources and configured to irradiate positions close to each other or the same position on the Fabry-Perot sensor with synthesized rays of light.

10. The acoustic signal receiving apparatus according to claim 1 wherein the first and second wavelengths are configured to be positioned in two different dips from among a plurality of dips of the reflectivity of the Fabry-Perot sensor.

11. The acoustic signal receiving apparatus according to claim 1, wherein a difference between the first wavelength and the second wavelength is 5 nm or more.

12. A photo-acoustic tomography comprising:

a photo-acoustic wave generating light source configured to irradiate the measurement object with light to cause a photo-acoustic wave to be generated;

acoustic signal receiving apparatus according to claim 1 configured to receive the photo-acoustic wave to acquire an acoustic wave signal; and wherein the processor generates tomographic image from the acoustic wave signal.

13. An acoustic signal receiving apparatus comprising:

a Fabry-Perot sensor including a Fabry-Perot interferometer configured to convert an acoustic wave generated from a measurement object to a light intensity signal;

a light source configured to emit light having a first wavelength and a second wavelength different from the first wavelength, wherein the first wavelength and the second wavelength are settable;

a detector configured to convert the light intensities of reflected rays of light obtained by irradiation of the Fabry-Perot sensor with rays of light from the light source into electric signals independently by the first wavelength and the second wavelength; and a processor configured to acquire a difference between an electric signal corresponding to the first wavelength and an electric signal corresponding to the second wavelength, wherein the first wavelength and the second wavelength are set so that differential values of reflectivity spectrum of the Fabry-Perot sensor are different at the first wavelength and the second wavelength.

14. The acoustic signal receiving apparatus according to claim 13, wherein the light source comprises:

a first light source configured to emit light having the first wavelength; and a second light source configured to emit light having the second wavelength.

15. The acoustic signal receiving apparatus according to claim 13, wherein the light source is a tunable light source configured to switch between emitting light having the first wavelength and the second wavelength.

16. The acoustic signal receiving apparatus according to claim 13, wherein:

the differential value of the reflectivity spectrum of the Fabry-Perot sensor at the first wavelength has a first sign; and the differential value of the reflectivity spectrum of the Fabry-Perot sensor at the second wavelength has a second sign that is opposite the first sign.

17. The acoustic signal receiving apparatus according to claim 16, wherein:

the reflectivity spectrum of the Fabry-Perot sensor includes a first dip that is a first local minimum value and a second dip that is also a second local minimum value;

the first wavelength is closer to the first dip than the second dip; and the second wavelength is closer to the second dip than first the dip.

* * * * *